US008070687B2

(12) United States Patent
Cinti

(10) Patent No.: US 8,070,687 B2
(45) Date of Patent: Dec. 6, 2011

(54) APPARATUS AND METHOD FOR DETECTING THE REPRODUCTIVE STATUS, IN PARTICULAR THE OESTRUS CYCLE, OF A MAMMAL

(75) Inventor: Enrico Cinti, Piacenza (IT)

(73) Assignee: Enrico Cinti, Piancenza (IT)

( * ) Notice: Subject to any disclaimer, the term of this patent is extended or adjusted under 35 U.S.C. 154(b) by 579 days.

(21) Appl. No.: 11/995,467

(22) PCT Filed: Jul. 13, 2006

(86) PCT No.: PCT/EP2006/006879
§ 371 (c)(1),
(2), (4) Date: Apr. 15, 2008

(87) PCT Pub. No.: WO2007/006579
PCT Pub. Date: Jan. 18, 2007

(65) Prior Publication Data
US 2008/0228058 A1 Sep. 18, 2008

(30) Foreign Application Priority Data
Jul. 13, 2005 (IT) .............. MI2005A1328

(51) Int. Cl.
*A61B 10/00* (2006.01)
*A61B 5/02* (2006.01)
*A61B 5/103* (2006.01)
*A61B 5/117* (2006.01)
(52) U.S. Cl. ............... 600/551; 600/504; 600/591
(58) Field of Classification Search .............. 600/551, 600/558, 591, 504, 505
See application file for complete search history.

(56) References Cited

U.S. PATENT DOCUMENTS

| 4,119,089 | A | | 10/1978 | Preti et al. | |
|---|---|---|---|---|---|
| 4,541,439 | A | * | 9/1985 | Hon | 600/504 |
| 4,757,823 | A | | 7/1988 | Hofmeister et al. | |
| 4,869,260 | A | | 9/1989 | Young et al. | |
| 5,417,207 | A | * | 5/1995 | Young et al. | 600/323 |
| 5,766,127 | A | * | 6/1998 | Pologe et al. | 600/310 |
| 5,782,778 | A | | 7/1998 | De Briere et al. | |
| 6,163,715 | A | * | 12/2000 | Larsen et al. | 600/323 |
| 2002/0156394 | A1 | | 10/2002 | Mehrotra et al. | |

FOREIGN PATENT DOCUMENTS

| EP | 0 132 119 A2 | 1/1985 |
|---|---|---|
| EP | 0 339 092 A1 | 11/1989 |
| JP | 2004105682 A | 4/2004 |
| WO | WO 99/35968 A1 | 7/1999 |

OTHER PUBLICATIONS

Pras, Elisabeth et al., "Pilot study of vaginal plethysmography in women treated with radiotherapy for gynecological cancer", Gynecologic Oncology, Dec. 2003, vol. 91, No. 3, pp. 540-546, XP-002401409, ISSN: 0090-8258.

* cited by examiner

*Primary Examiner* — Max Hindenburg
*Assistant Examiner* — John Pani
(74) *Attorney, Agent, or Firm* — Shoemaker and Mattare

(57) ABSTRACT

An apparatus for detecting the reproductive status, in particular the oestrus cycle, of a mammal, comprising detecting means (10) to detect a blood amount perfused in a predetermined region of the vagina canal of a mammal, and generating a corresponding main signal (20); the apparatus (1) further comprises a processing unit (40) associated with said detecting means (10) to determine the reproductive status of said mammal depending on said main signal (20). Also disclosed is a method of detecting the reproductive status, in particular the oestrus cycle, of a mammal.

5 Claims, 11 Drawing Sheets

FIG 2
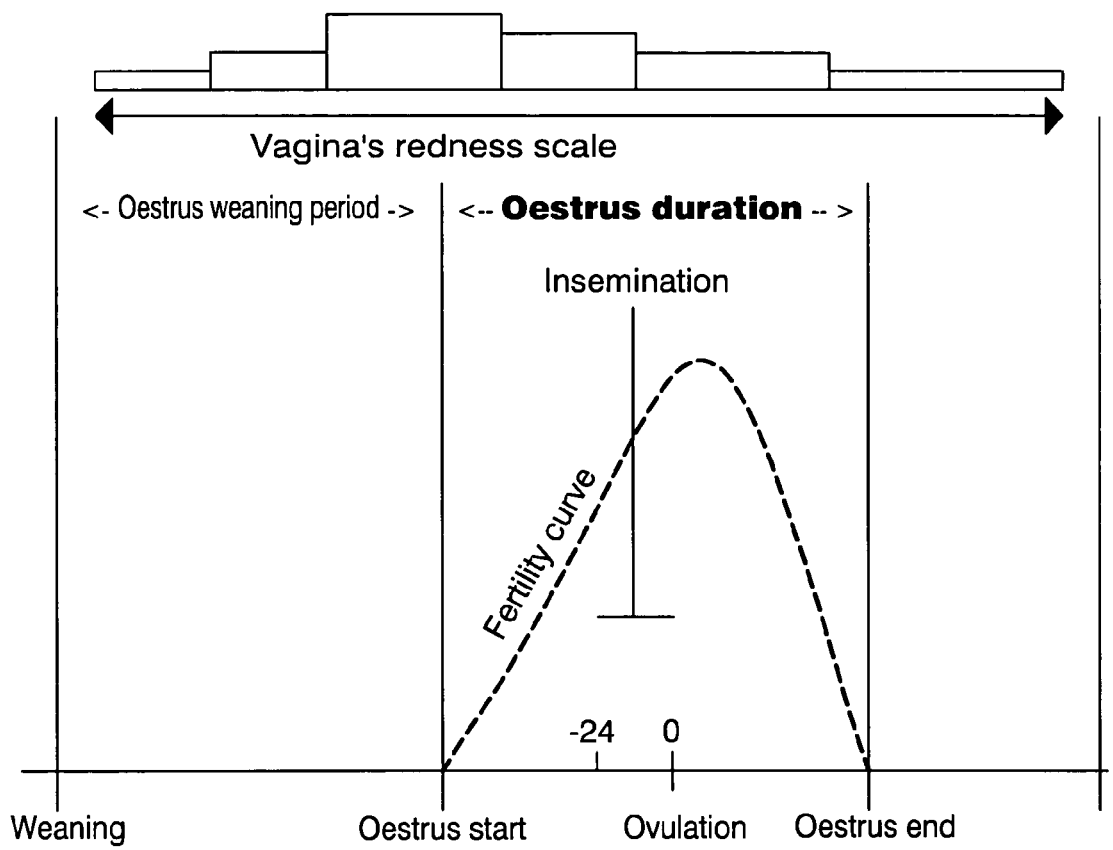
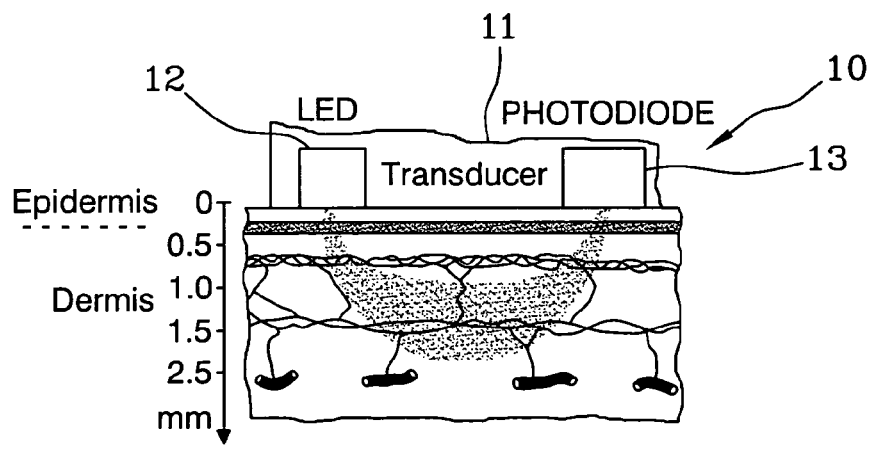
FIG 3

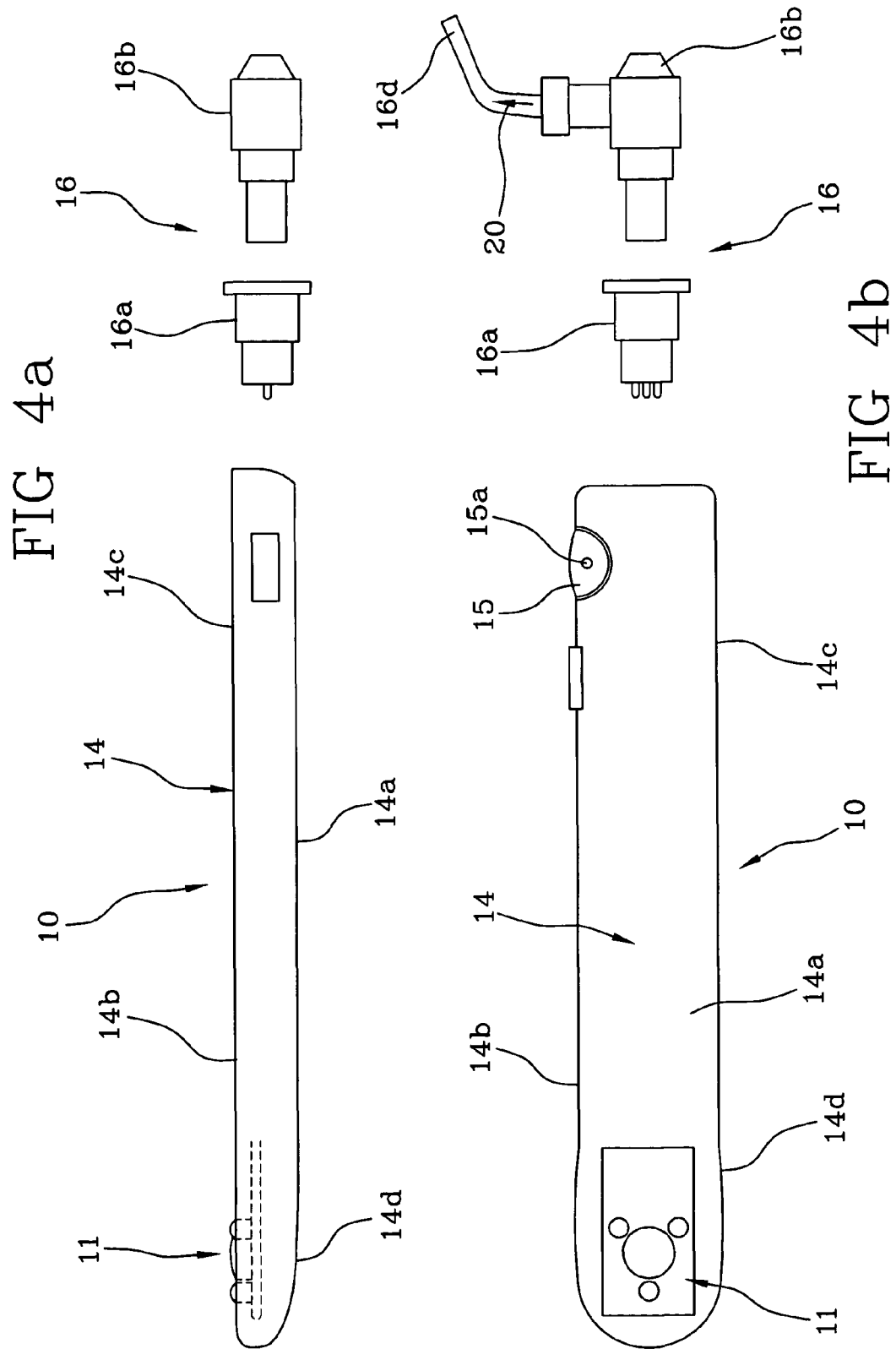

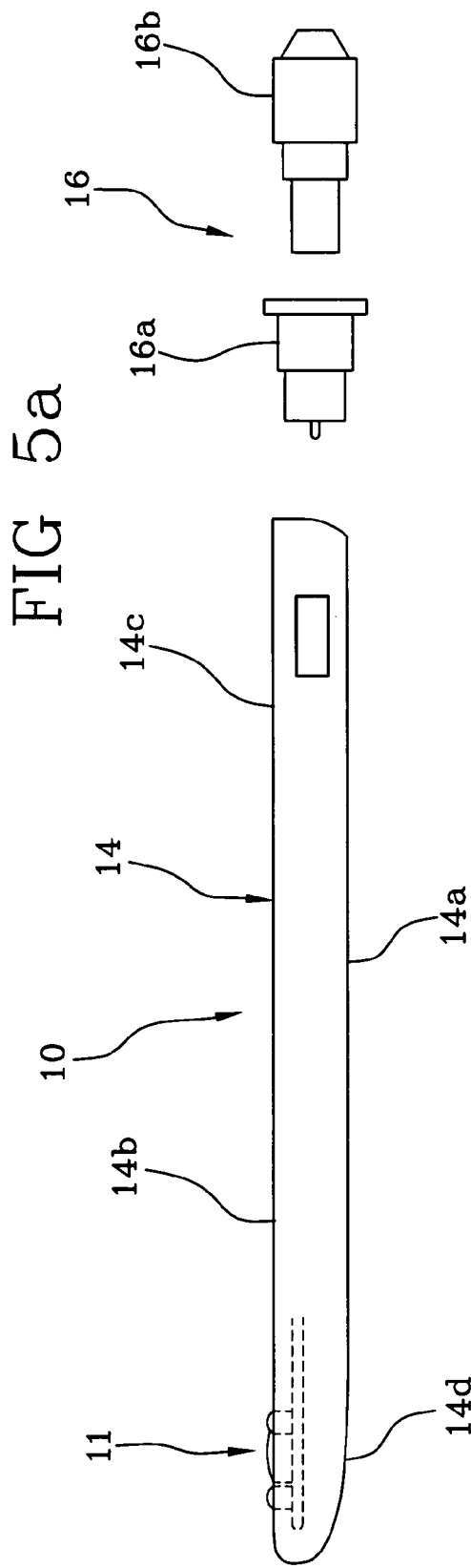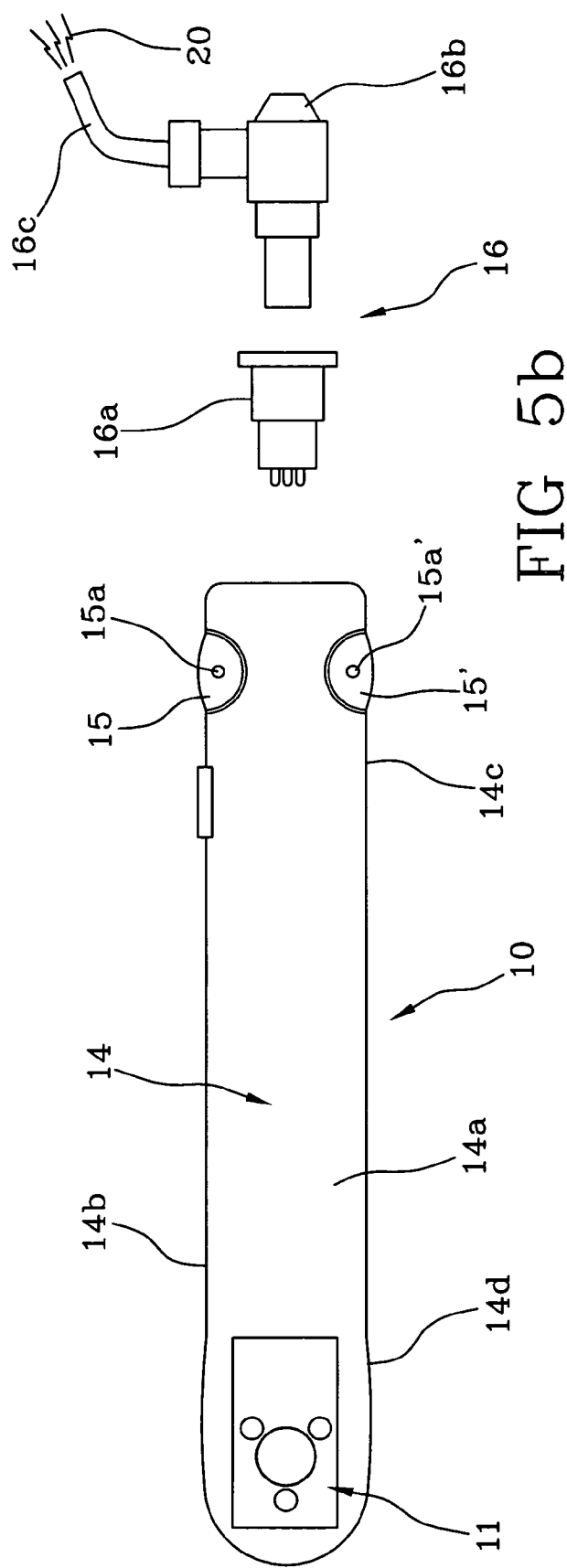
FIG 5a
FIG 5b

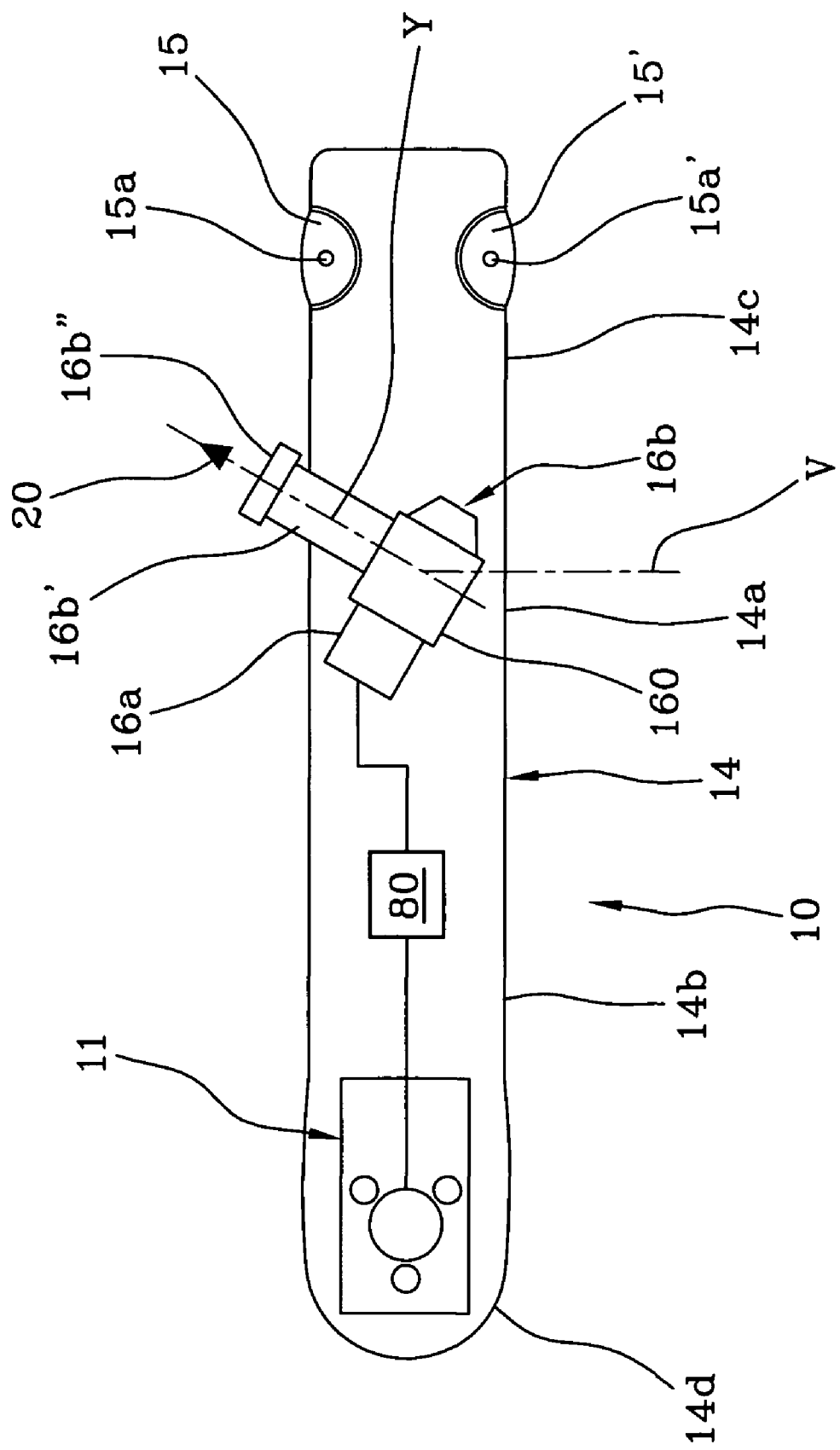

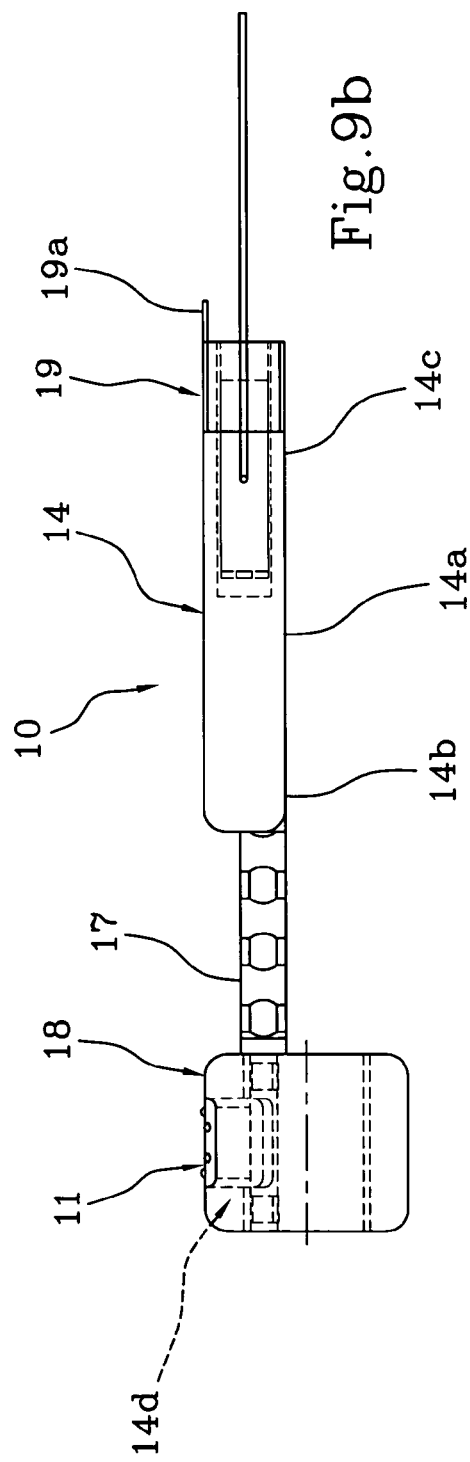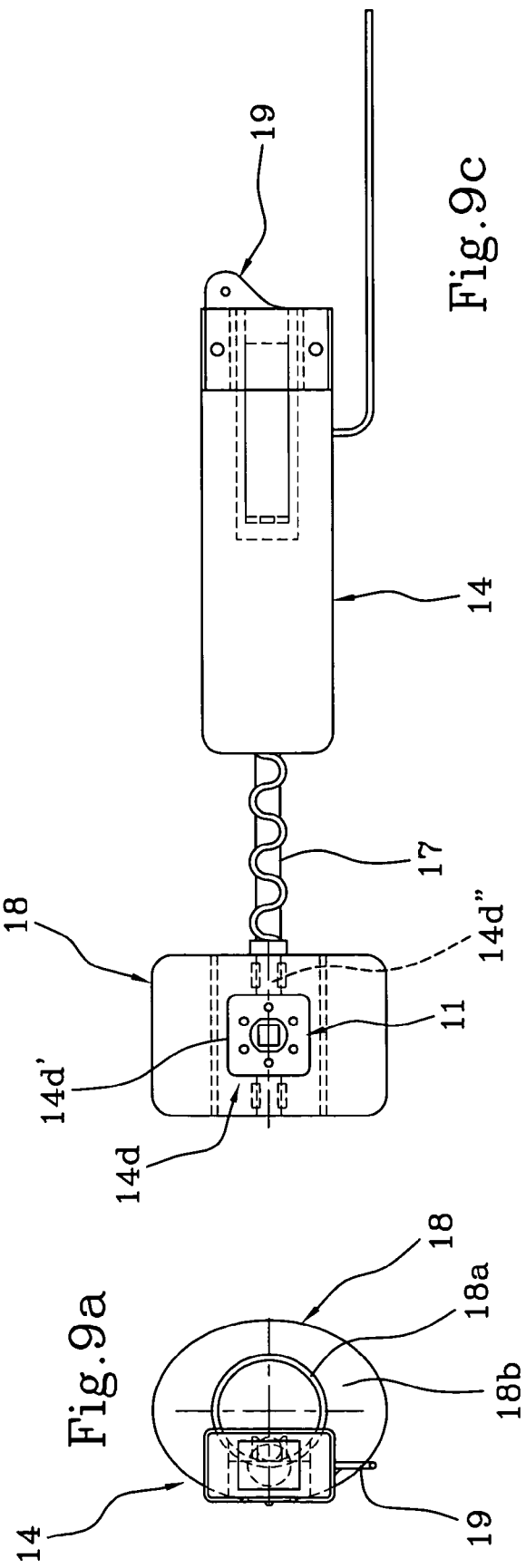

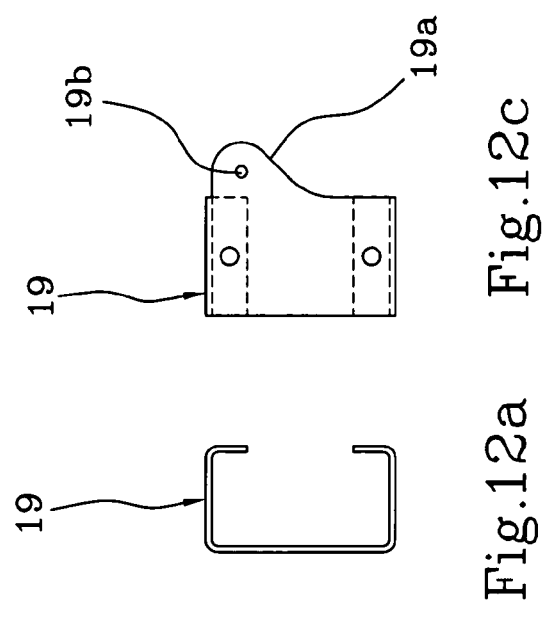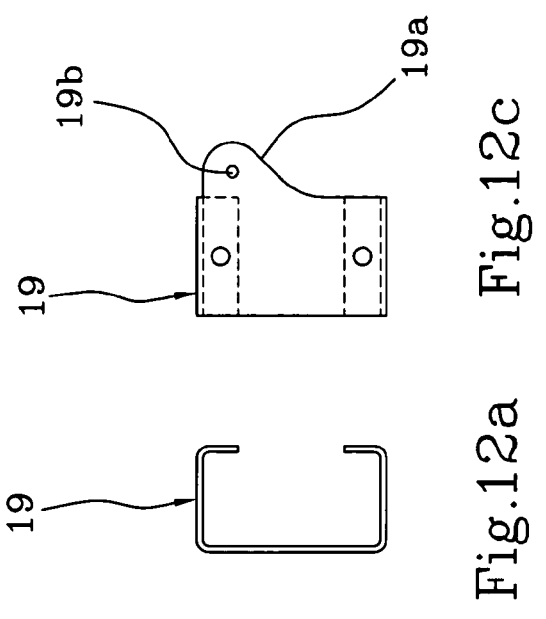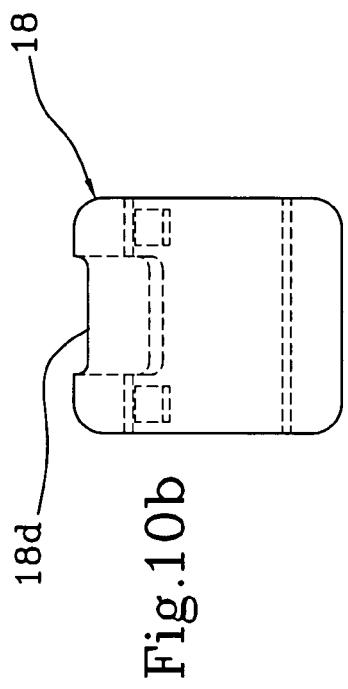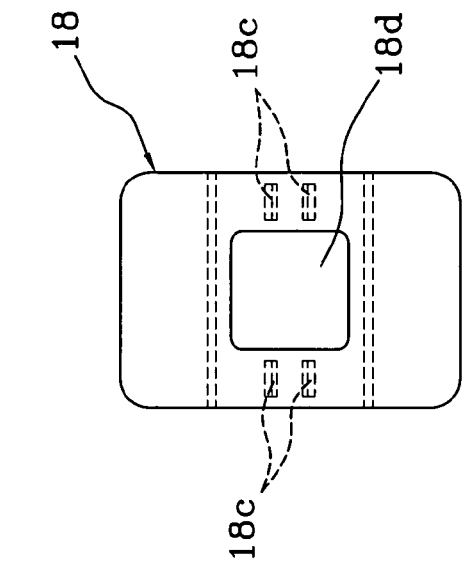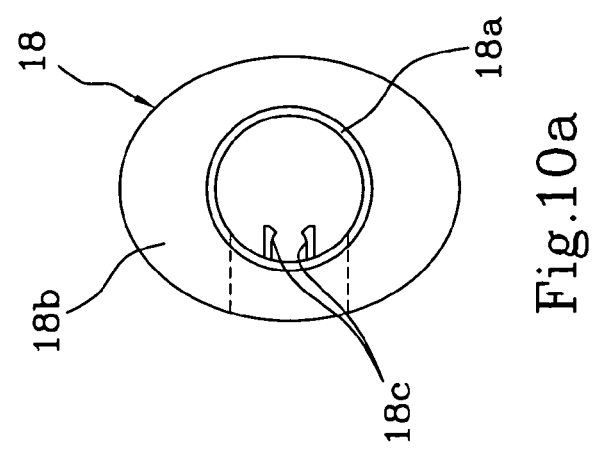

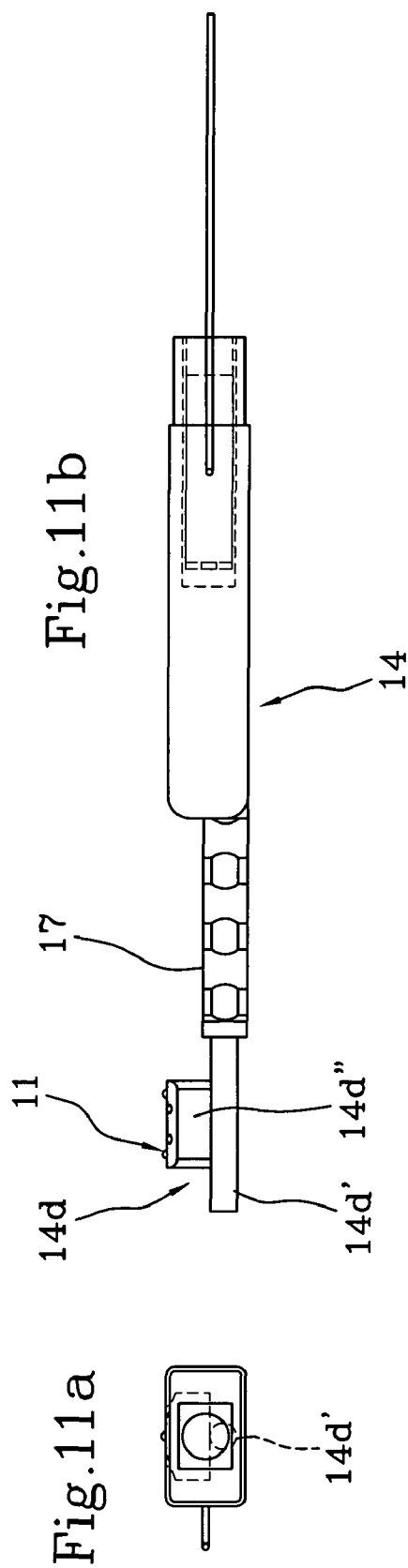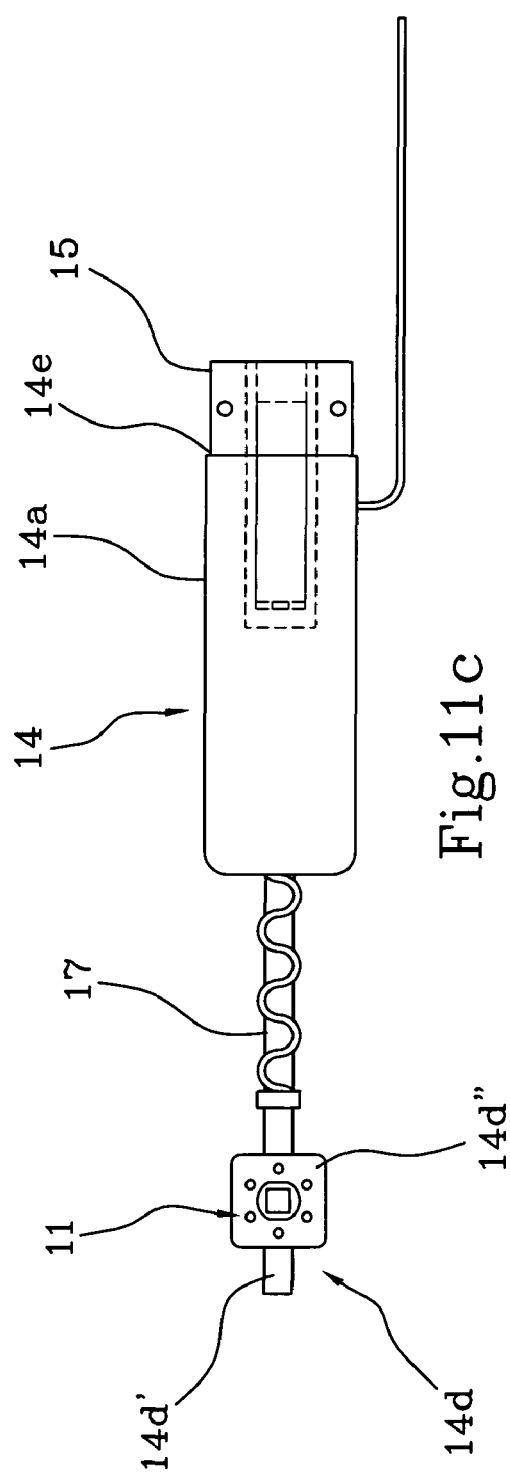

APPARATUS AND METHOD FOR DETECTING THE REPRODUCTIVE STATUS, IN PARTICULAR THE OESTRUS CYCLE, OF A MAMMAL

The present invention relates to an apparatus and a method of detecting the reproductive status, in particular the oestrus cycle, of a mammal.

It is known that stockbreeders' success and profits mostly depend on the capability of producing a large, numerous and viable offspring of the animals they are breeding.

Therefore, increasing of the birthrate by ensuring the highest percentage of fecundation of the mature ovules is desirable. In fact, an untimely or premature insemination is the main cause of infertility, in particular in pig production.

The period during which a female accepts a male is generally referred to as "heat".

In particular, within the pig species the period of heat has a duration included between 18 and 24 days, for an average of about 21 days; this heat period comprises two phases: the pro-oestrus and oestrus phases (the last one being indicated as the true heat period); the oestrus phase is the period during which ovulation occurs in sows. Identification of the oestrus period (start and end) is presently carried out through observation of the behavioural and visual changes in the animal, or through monitoring of the ovarian steroids.

In the first case, it is the stockbreeder himself/herself who is entrusted with the task of noticing one or more of the following factors, typically connected with the animal's fertility period:
  redness of the vulva labia and swelling of the latter;
  the produced mucus is filamentous and may become viscous;
  irregular appetite;
  increased restlessness accompanied by particular grunts;
  ear straightening (for breeds with erect ears);
  tendency to "rubbing";
  immobility following pressure received on the back;
  copulation acceptance;
  attraction towards the male;
  tendency to turn over if the animal is in a cage.

It is clear that determining the animal's oestrus phase exclusively on the basis of observations carried out by the operators in charge, has different drawbacks.

First of all, in order to provide reliable indications, the operator must have great experience in the sector; therefore highly qualified staff is required for detection, since inexperienced collaborators for example are unable to conduct this type of detection.

In addition, the animals' observation must be carried out at least twice each day, which time is therefore subtracted to those experts who have more experience and, due exactly to their abilities, should be designed to also perform other different tasks.

Then, leaving out of consideration the observer's ability, the determination performed following the above listed criteria does not possess the necessary accuracy and reliability degree as required for an efficient optimisation of the resources and maximisation of the percentage of fertilised ovules following the insemination to be carried out afterwards.

As regards monitoring of the hormonal variations, it is to be pointed out that the serum levels of the gonadotropins as well as the sexual steroids such as estradiol and progesterone for example, can be used to emphasise the period at which ovulation takes place.

However, much time is required before the results of immunoassays/radioimmunoassays for determining said hormonal variations are available, and therefore this technique cannot be efficiently used as a routine in commercial cattle-breeding, for both technical and economic reasons.

FIG. 1 shows a graph of the production of reproductive hormones against time during the oestrus cycle of the pig species.

Ovulation takes place in a constant manner approximately at two thirds of the whole duration of the true heat (oestrus) period estimated with the immobility reflex.

However, since the oestrus duration is not constant (with an oscillation of 12 to 88 hours), this analysis only supplies an estimate a posteriori of the ovulation moment and therefore an evaluation subsequent to the useful period for insemination.

The artificial insemination in sows must take place within the 24 hours preceding ovulation, so that presently several inseminations are carried out, in order to approach this objective as much as possible, trying not to execute the last intervention too late in the ovulation period or at the end of the heat period, because this would reduce the fertilization rate and the number of new-borns.

Presently the insemination moment is selected based on the beginning of oestrus; however, ovulation takes place within a very variable period (10 to 85 hours) relative to the oestrus beginning.

Due to this incertitude, the beginning of oestrus is not a reliable factor for programming the processes of artificial insemination.

Accordingly, it is an aim of the present invention to provide an apparatus and a method of detecting the reproductive status, in particular the oestrus cycle, of a mammal, enabling the animal's reproductive status to be determined in a precise and reliable manner.

It is a further aim of the invention to make available an apparatus and a method of detecting the reproductive status, in particular the oestrus cycle, of a mammal enabling optimal insemination strategies to be adopted, so as to reduce the artificial-insemination costs and correspondingly increase the birthrate.

The foregoing and further aims are substantially achieved by the apparatus and the method in accordance with the features recited in the appended claims.

Further features and advantages will become more apparent from the detailed description of a preferred but not exclusive embodiment of the invention.

This description is taken with reference to the accompanying drawings, given by way of non-limiting example, in which:

FIG. 2 is a diagram representing an artificial-insemination strategy;

Figure 1:
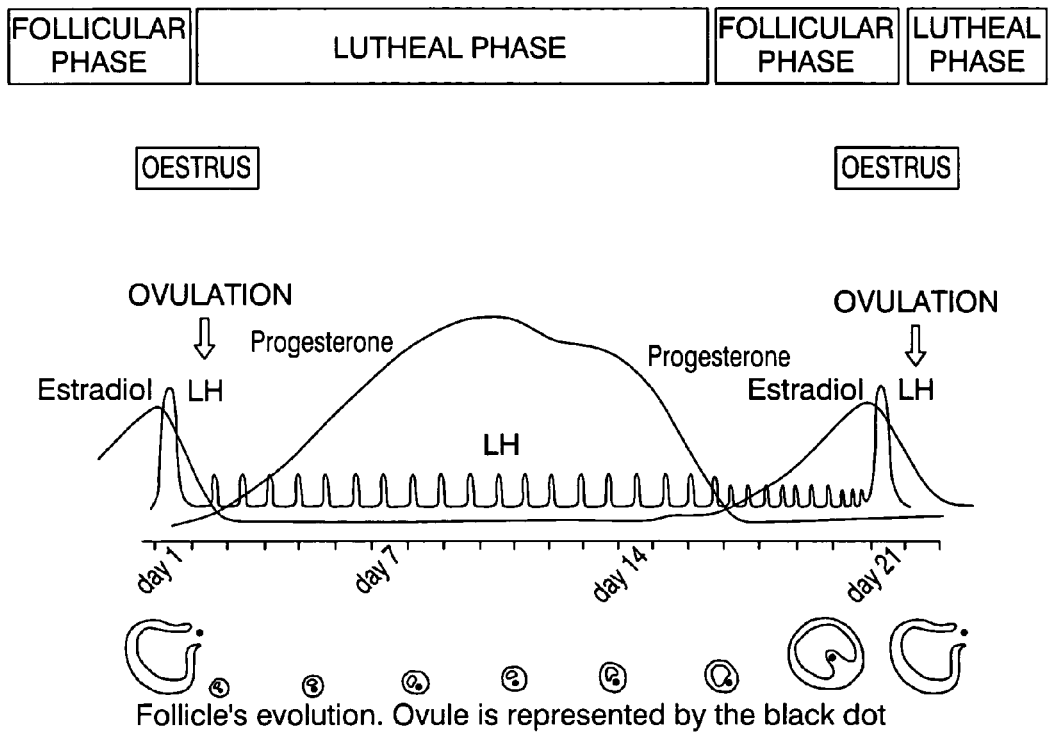
FIG. 1 is a graph showing the production of reproductive hormones towards time during the oestrus cycle in the pig species.
Figure 6:
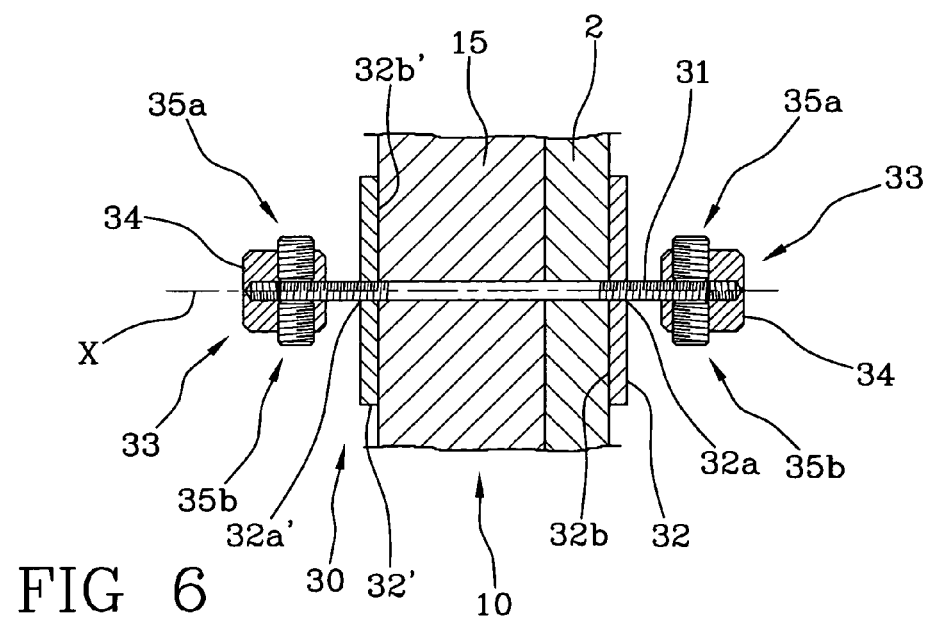
Figure 7:
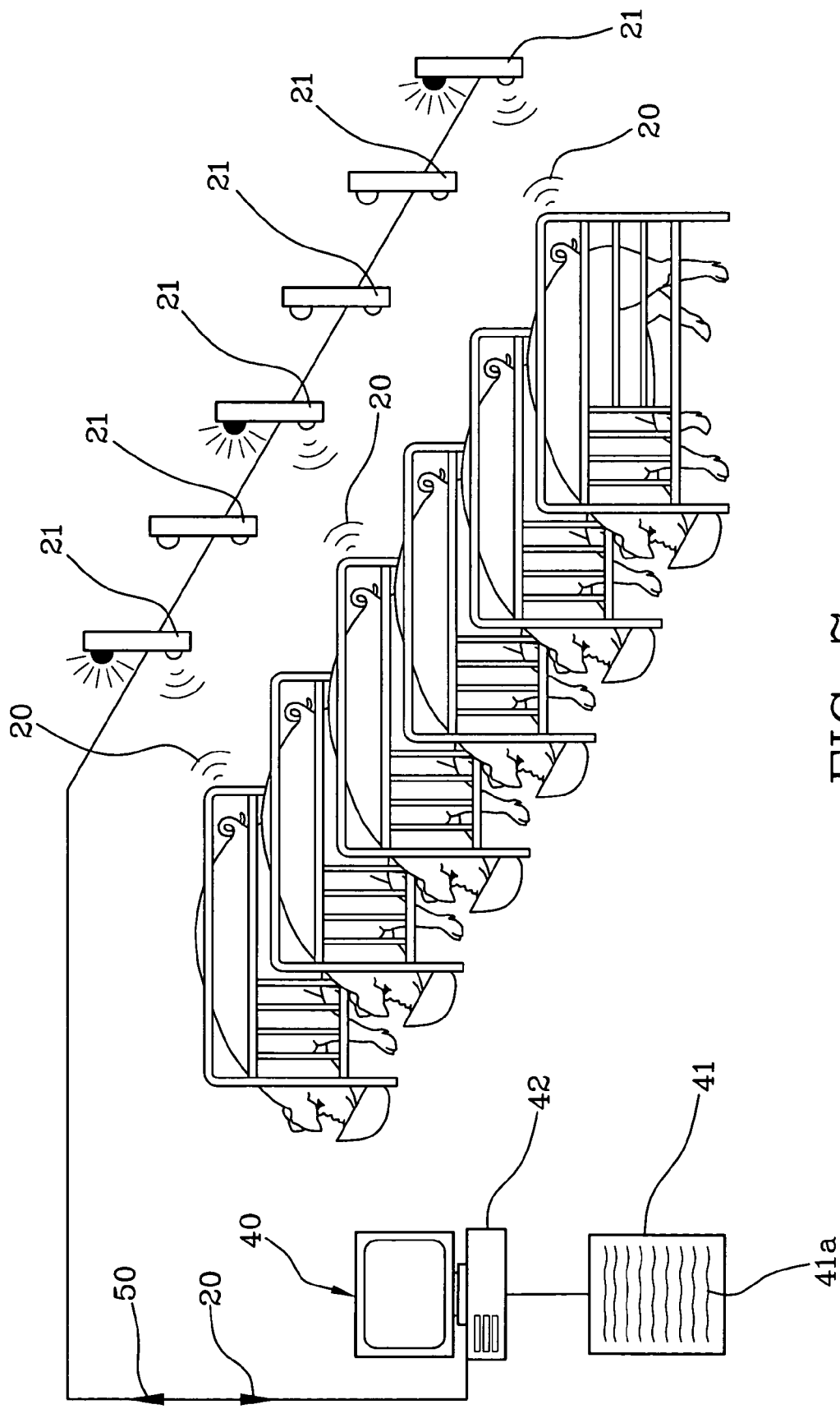
Figure 14:
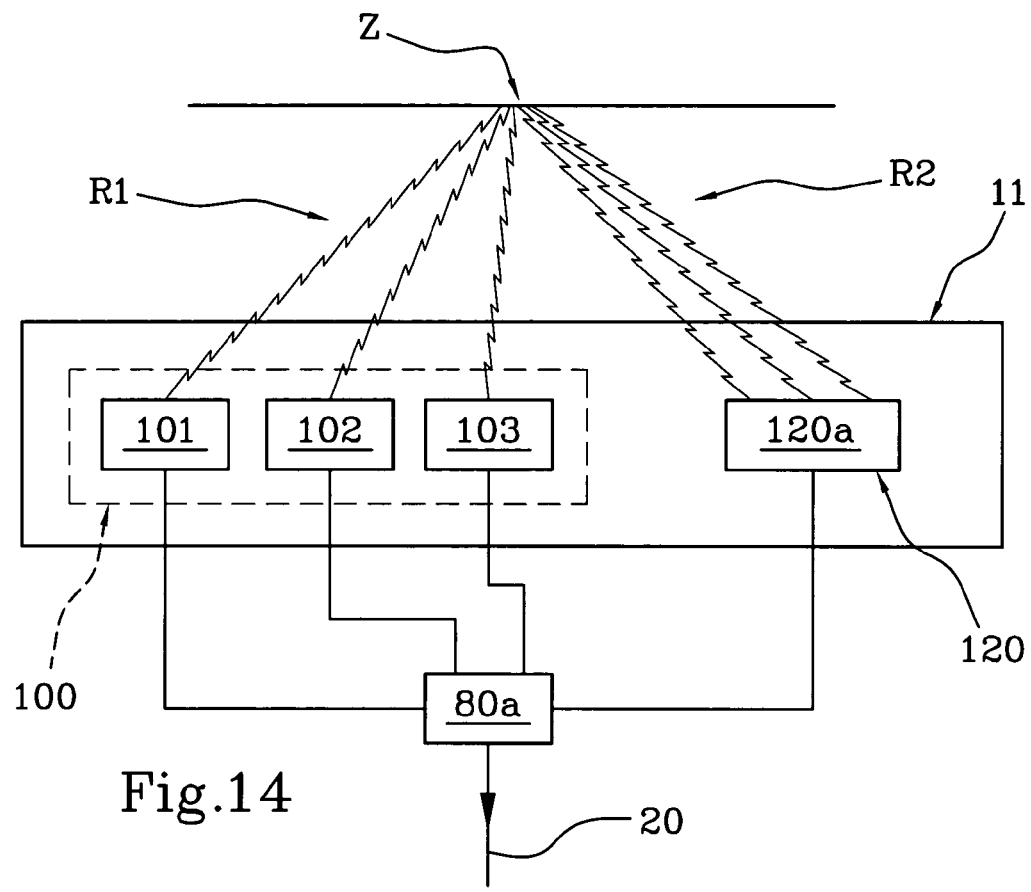
Figure 13:
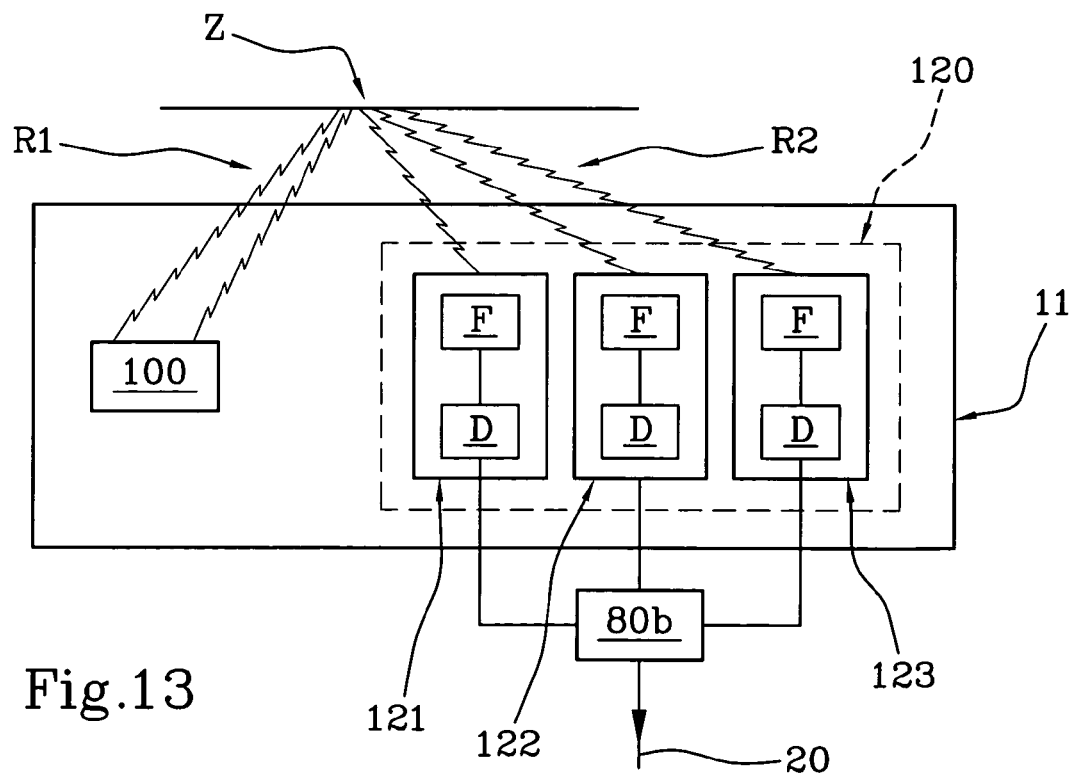
Figure 15:
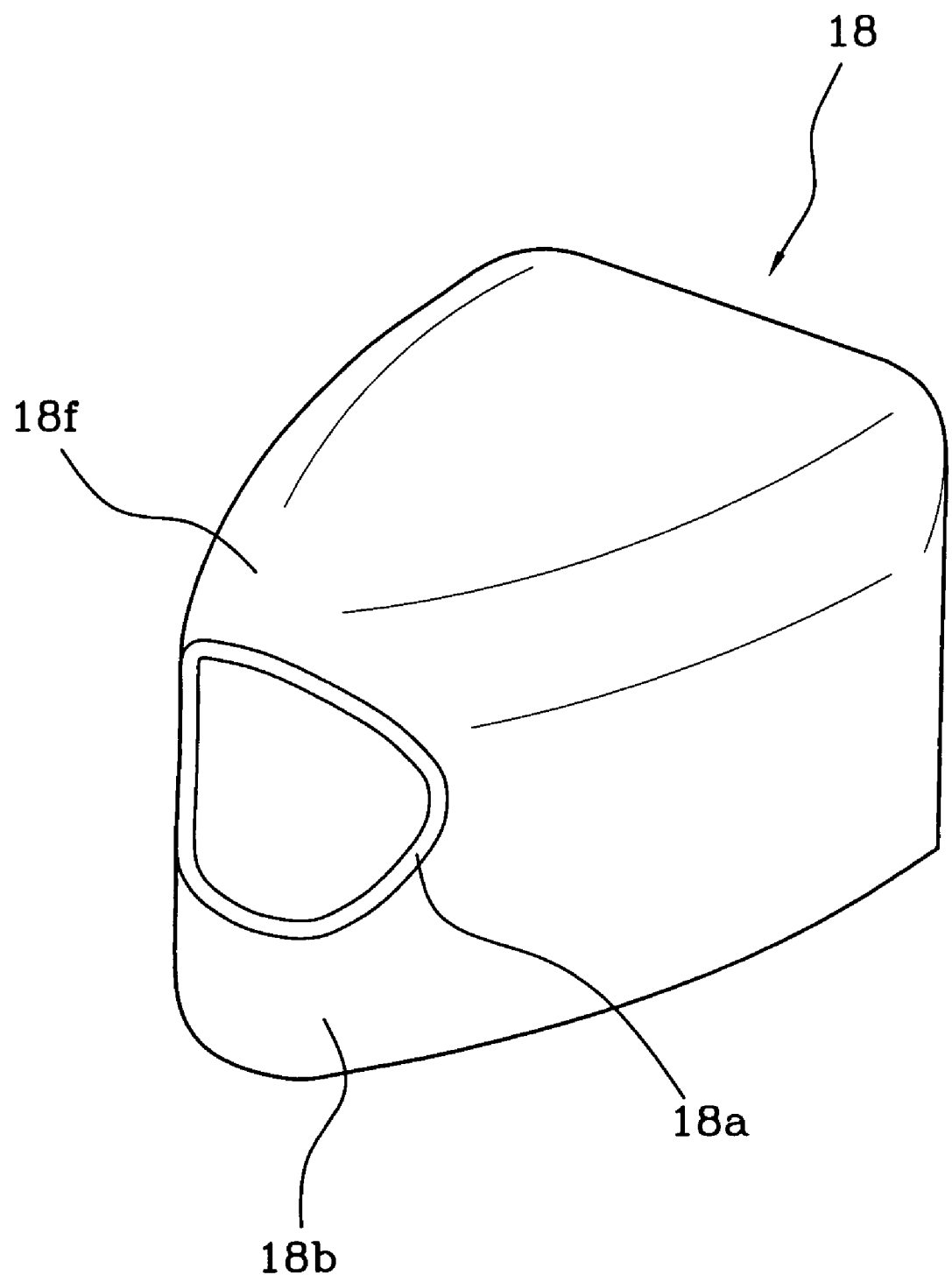

FIG. 3 diagrammatically shows a portion of the apparatus in accordance with the invention, in use;

FIG. 4a is a partly-exploded, diagrammatic side view of a first embodiment of another portion of the apparatus in accordance with the invention;

FIG. 4b is a partly-exploded, diagrammatic plan view of the portion shown in FIG. 4a;

FIG. 5a is a diagrammatic side view of a second embodiment of the portion seen in FIG. 4a;

FIG. 5b is a diagrammatic plan view of the portion seen in FIG. 5a;

FIG. 6 is a side view of a further detail of the apparatus in accordance with the invention;

FIG. 7 shows the apparatus of the invention in use;

FIG. 8 diagrammatically shows the apparatus portion seen in FIGS. 4a, 4b, 5a and 5b in an assembled condition and in plan view;

FIGS. 9a, 9b and 9c show a front view, side view and plan view respectively of an alternative embodiment of the apparatus portion seen in FIG. 8;

FIGS. 10a, 10b, 10c are a front view, side view and plan view respectively of a first detail of the apparatus portion shown in FIGS. 9a, 9b, 9c;

FIGS. 11a, 11b, 11c are a front view, side view and plan view respectively of a second detail of the apparatus portion shown in FIGS. 9a, 9b, 9c;

FIGS. 12a, 12b, 12c are a front view, side view and plan view respectively of a third detail of the apparatus portion shown in FIGS. 9a, 9b, 9c;

FIG. 13 is a block diagram of a first embodiment of a detail of the apparatus portion shown in FIGS. 4a, 4b, 5a, 5b, 8, 9a-9c, 10a-10c, 11a-11c, 12a-12c;

FIG. 14 is a block diagram of a second embodiment of a detail of the apparatus portion shown in FIGS. 4a, 4b, 5a, 5b, 8, 9a-9c, 10a-10c, 11a-11c, 12a-12c;

FIG. 15 diagrammatically shows an alternative embodiment of a structural element of FIGS. 9a-9c and 10a-10c.

With reference to the drawings, an apparatus for detecting the reproductive status, in particular the oestrus cycle, of a mammal in accordance with the present invention has been generally identified with 1.

Apparatus 1 applies in the breeding field, and in particular as far as breeding of pigs, oxen, buffaloes and the like is concerned; obviously, apparatus 1 can be also used for any other mammal species, preferably mammals kept for breeding.

Apparatus 1 comprises detecting means 10 to detect an amount of blood perfused in a predetermined region Z of the vagina canal of the mammal under observation.

The detecting means 10 generates a main signal 20 representing this blood amount.

Practically, the detecting means 10 may comprise a sensor 11, preferably of the plethysmographic type (FIGS. 3, 4a, 4b, 5a, 5b, 9a-9c, 11a-11c, 13, 14); the sensor task is to detect the amount and type of light that is reflected by the predetermined region Z of the vagina canal (representative of the blood amount perfusing the vagina mucous membrane) so as to enable quantification and processing of the redness degree by a processing unit 40 to be better described in the following, together with the preferred embodiments of sensor 11.

Under use conditions, the detecting means 10 is inserted at least partly into the mammal's vagina canal, so that the necessary detecting operations can be carried out in a correct and reliable manner.

The detecting means 10 may comprise a housing 14 holding the circuitry necessary to perform at least the operations for detection. Housing 14 preferably has an elongate shape to enable it to be easily inserted into the mammal's vagina canal; by way of example, housing 14 may have an axial length (i.e. along the insertion direction in the mammal's vagina canal) included between 4 and 20 cm, depending on the length of the vagina canal.

The housing 14 has a first portion 14a and a second portion 14d; the latter may contain the sensor 11. The first portion 14a has a first end 14b at which the second portion 14d is positioned, and a second end 14c at which connecting means 16 is mounted, which means enables supply of the main signal 20 to the rest of apparatus 1.

Housed in the first portion 14a is the hardware (generally denoted at 80) which is required for processing the magnitudes detected by sensor 11 and obtaining the main signal 20.

FIGS. 4a, 4b, 5a and 5b in particular show an exemplary conformation of housing 14 substantially made of a single body.

As shown in the exploded view of FIGS. 4a, 4b, 5a, 5b, the connecting means 16 comprises a three-pole connector 16a and an L-shaped connector 16b.

In the embodiment in FIGS. 4a, 4b, a wire 16d is connected to connector 16b to transmit the main signal 20 to the remaining devices of apparatus 1.

In the embodiment shown in FIGS. 5a, 5b, an antenna 16c for communication of the wireless type is connected to connector 16b; note that in reality the length of the antenna 16c can be even greater than 8-10 cm and that, for the sake of clarity, said antenna 16c has not been shown to scale with the rest of the figure.

The housing 14 is made of a washable and non porous plastic material so that it can be easily introduced into the animal's vagina canal.

FIG. 8 shows the detecting means 10 of FIGS. 4a, 4b, 5a, 5b in which the connectors 16a, 16b are mounted within the housing 14; in particular, these connectors 16a, 16b are positioned between the hardware block 80 and the engagement portion 15 to be better described in the following.

In an alternative embodiment (FIGS. 9a-9c, 10a-10c, 11a-11c), the housing 14 comprises a flexible elongated element 17 preferably made of elastomer material to connect the second portion 14d and the first portion 14a (in particular the first end 14b) of the housing 14 itself with each other.

In more detail, the second portion 14d of housing 14 can be provided (FIGS. 9a-9c, 11a-11c) with an elongated portion 14d' and a radial expansion 14d" on which sensor 11 is mounted.

Apparatus 1 further comprises a tubular structure 18 having a substantially cylindrical or elliptical conformation for example, which in turn includes a first tubular body 18a that is radially internal and substantially rigid, and a second tubular body 18b that is radially external and is made of elastomer material or more generally a flexible material.

Extending in the radially internal region delimited by the first tubular body 18a, starting from an inner surface of the first tubular body 18a, is at least one pair of expansions 18c for engagement, by snap fitting for example, with the elongated portion 14d' of the second portion 14d of housing 14.

Preferably two pairs of expansions 18c are provided and they extend internally of the inner surface of the first tubular body 18a, said pairs being positioned on axially opposite sides with respect to the second portion 14d of housing 14 to engage the elongated portion 14d'.

Advantageously, the region that is internally defined by the first tubular body 18a has sizes large enough to house the second portion 14d of housing 14. In other words, the first tubular body 18a is such conceived that the second portion 14d can be axially inserted in the inner region of said first tubular body 18a and the expansions 18c can be engaged with the elongated portion 14d' of the second portion 14d itself.

The tubular structure 18 has an opening 18d on its side surface, so that sensor 11 can at least partly face the predetermined region Z of the vagina canal; in particular, following mounting of the tubular structure on the second portion 14d of housing 14, sensor 11 is in register with said opening 18d and preferably is at least partly inserted therein.

Advantageously, the interference existing between sensor 11 and opening 18d on the side surface of the tubular structure helps in preventing mutual axial sliding between the second portion 14d (and therefore the sensor 11 itself) and the tubular structure 18.

The main task of the tubular structure 18 is to keep sensor 11 in place within the mammal's vagina canal, so that the detection carried out can be accurate and reliable.

Further, the internal cavity of the first tubular body 18a is useful for allowing the insertion of a catheter to carry out an artificial insemination operation.

Preferably, the tubular structure 18 has an outer surface having a non-cicrcular cross section, as shown in FIGS. 9a and 10a, so as to avoid rotations of the tubular structure 18, and of the sensor 11, around the longitudinal axis of the tubular structure 18.

Preferably, the tubular structure 18 has a tapered end 18f (FIG. 15) decreasing its cross section on moving away from the first portion 14a of the housing 14, so as to facilitate the insertion of the tubular structure 18 into the vagina canal.

It is to be noted that the second portion 14d of the housing 14 may be engaged to the tubular structure in other manners; for example, the elongated portion 14d' can be fixed to the external surface of the tubular structure 18.

By means of the elongated element 17, a partial relative displacement between the second and first portions 14d, 14a of housing 14 is allowed so as to enable apparatus 1 to adapt itself to the conformation of the vagina canal of the animal under examination. In other words, also following unavoidable movements of the animal, thanks to the above described structure, sensor 11 is maintained to the correct position so that determination of the mammal's oestrus cycle is in any case reliable.

The electrical connection between the sensor 11 and the hardware mounted within the first portion 14a of the housing 14 can be obtained by means of one or more cables placed within a tubular longitudinal internal cavity of the elongated element 17.

As above said, housing 14 can house at least the sensor 11. For maintaining the detecting means 10 to the correct position for carrying out the functions they must perform, apparatus 1 comprises fastening means 30 (FIG. 6) to secure the detecting means 10 to the mammal's vagina canal.

The fastening means 30 comprises a main body 31, preferably having a rod-like conformation and extending along a respective longitudinal axis X. The main body 31 is adapted to be inserted into a hole formed in a vagina labium of the mammal to define a link between said labium 2 and the detecting means 10. In particular, this hole can be formed in the upper portion of one of the two vagina labia of the mammal; in other words the hole is not formed at the base of this vagina labium.

In this manner, the hole is formed in the vagina labium portion that is most provided with elastic tissue rather than with fibrous tissue, so that the risk of infections is minimised.

By way of example, the hole can be formed to a distance of about 1-2 centimetres from the union point of the vagina labium.

The fastening means 30 further comprises a contact element 32 having an abutment surface 32b bearing against the mammal's vagina labium; preferably the contact element 32 has a plate-like conformation.

The contact element 32 further has a through hole 32a preferably at a substantially central position, into which the main body 31 is introduced.

It is to be noted that also an auxiliary contact element 32' can be used, which auxiliary contact element has an abutment surface 32b' bearing against an engagement portion 15 of the detecting means 10; the auxiliary contact element 32' too preferably has a plate-like conformation.

The auxiliary contact element 32' also has a through hole 32a' at a substantially central position, into which the main body 31 is introduced.

The fastening means 30 further comprises a closing member 33 associated with at least one axial end of the main body 32 to keep the detecting means 20 in engagement with the mammal's vagina labium.

In more detail, the closing member 33 comprises a pair of nut elements 34 each associated with a respective axial end of the main body 31 and slidable along said main body.

Also provided is at least one pair of headless screws 35a, each operatively associated with a respective nut element 34 to secure said nut element to the main body 31.

In the preferred embodiment provision is also made for a further pair of headless screws 35b to make the mutual engagement between the main body 31 and nut elements 34 more reliable.

Advantageously, the detecting means 10 has an engagement portion 15 provided with a through hole 15a into which the main body 31 of the fastening means 30 is inserted. Preferably, the engagement portion 15 is a portion of housing 14.

In the embodiment in FIGS. 5a, 5b (typically dedicated to wireless transmissions) the detecting means 10, and in particular the housing 14, can be also provided with an auxiliary annular portion 15' having a through hole 15a'; in this way the operator is allowed to select the orientation in which the detecting means 10 is to be disposed within the animal's vagina canal.

It is to be noted that FIG. 8 refers both to the embodiment shown in FIGS. 4a, 4b and to the embodiment seen in FIGS. 5a, 5b; therefore the housing has been represented with both the engagement portions 15, 15'. Obviously, if the embodiment of FIGS. 4a, 4b is considered, the housing 14 will be provided with the engagement portion 15 alone.

As an alternative to the holes shown in FIGS. 4a-4b, 5a-5b and 8, the engagement portion 15 may show a narrowing part (i.e. a portion of reduced cross-section) defining a shoulder 14e together with the first portion 14a; abutting thereon is a locking element 19 of a substantially annular or C-shaped conformation (FIGS. 9a-9c, 11a-11c, 12a-12c).

The locking element 19 has a lug 19a having a through hole 19b for engagement with a vagina labium of the animal under examination, through the above described fastening means 30, for example; in particular, the main body 31 of the fastening means 30 can be inserted in the through hole 19b of said lug 19a in order to obtain such engagement.

The shape of the inner surface of the locking element 19 substantially matches that of the outer side surface of the narrowing part of the engagement portion 15, so that the locking element 19 itself can be fitted on the engagement portion 15.

Fastening between the locking element 19 and engagement portion 15 can be obtained through conventional means, such as screws for example.

Note that the engagement portion shown in FIGS. 4a-4b, 5a-5b and 8 can also be used in the embodiment with the housing 14 as shown in FIGS. 9a-9c, 11a-11c, 12a-12c and, vice versa, the engagement portion and locking element shown in FIGS. 9a-9c, 11a, 11c, 12a-12c can be also used in the embodiment with the housing 14 as shown in FIGS. 4a-4b, 5a-5b and 8.

FIG. 8 shows how the outlet portion 16b' of connector 16 preferably extends along a longitudinal axis Y, which axis is inclined through a non-zero angle relative to the axis V perpendicular to the longitudinal extension of housing 14.

In more detail, the connector 16b is such inclined that its outlet portion 16b' extends away from the second portion 14d of housing 14 and at least partly directs an outlet mouth 16" thereof towards the engagement portion 15. In other words, the outlet mouth 16b" is disposed farther away from sensor 11 than a junction region 160 defined between the L-shaped connector 16b and connector 16a.

Practically, when the detecting means 10 must be fastened to the mammal's vagina canal, the following steps are carried out:

- forming a through hole in a vagina labium 2 of the mammal (preferably at the above stated position);
- inserting the main body 31 into said through hole;
- bearing the abutment surface 32b of the contact element 32 against the mammal's vagina labium, through insertion of the main body 31 into the through hole 32a of the contact element 32 itself;
- abutting the engagement portion 15 of the detecting means 10 (or the lug 19a of the locking element 19) against the mammal's vagina labium 2, on the opposite side relative to the contact element 32, the main body 31 being inserted into the through hole 15a (or 19b);
- causing sliding of the nut elements 34 along the main body 31, until mutual fastening between the above mentioned elements is achieved;
- locking the position of said nut elements 34 through the headless screws 35a and the headless screws 35b if use of the latter is provided.

In case of use of the auxiliary contact element 32' as well, the latter is mounted on the main body 31 (through insertion of the latter into the through hole 32a' of the auxiliary contact element 32') at the opposite axial end with respect to the contact element 32.

Practically, while the contact element 32 abuts against the mammal's vagina labium 2, the auxiliary contact element 32' has an abutment surface 32b' bearing against the engagement portion 15 of the detecting means 10 (or the lug 19a of the locking element 19).

It is apparent that the above stated steps must not be necessarily performed following the above specified order; it is only important that at least one of the nut elements 34 be mounted on the main body 31 after the latter has been introduced into the through hole 32a of the contact element 32, the hole formed in the animal's vagina labium, the through hole 15' of the engagement portion 15 of the detecting means 10 (or the through hole 19b of said lug 19) and possibly the through hole 32a' of the auxiliary contact element 32'.

It is to be pointed out that the fastening means 30 can be also employed with other types of sensors and devices suitable for engagement with the vagina canal of an animal.

By virtue of the hitherto described structure, the detecting means 10 therefore is able to reliably detect the amount of blood perfused in a predetermined region of the mammal's vagina canal and to generate the corresponding main signal 20.

The main signal 20 is transmitted to a processing unit 40 (FIG. 7) whose function is to determine the reproductive status of the mammal depending on the main signal 20 itself.

In particular, an interface 21 carries out amplification and filtering of the main signal 20 so that the latter is adapted to be transmitted to the processing unit 40 and to be submitted to the subsequent processing operations.

Conveniently, the processing unit 40 comprises a memory 41 in which one or more reference parameters 41a for the reproductive state of the mammal under observation are stored; these reference parameters 41a for example represent typical values of the redness levels of the animal's vulva during the oestrus period.

These values can refer in an equivalent manner to the amount of blood perfused in the inner surface of the animal's vagina canal; in fact, as above stated, the amount of redness of the animal's vulva area and the amount of blood flowing into the vagina canal are two magnitudes that are strictly connected with each other.

The processing unit 40 further comprises a comparison block 42 associated with memory 41 to compare one or more reference parameters 41a with the main signal 20. In this way, the reproductive status of the mammal can be determined and the subsequent steps for artificial insemination can be programmed.

In other words, the comparison carried out by the comparison block 42 aims at verifying whether the magnitudes incorporated in the main signal 20 (vulva redness level/perfused-blood amount) substantially correspond to the previously stored reference values; if that is so, there is a very high chance of the animal being in the fertile period and therefore the insemination procedure can be put into practice.

In more detail, the processing unit 40 is provided with a control software that, depending on the data received through the main signal 20, is able to predict the ovulation moment in a very reliable manner, thus enabling a careful programming of the artificial insemination activity.

The reference parameters 41a considered for processing can refer to the overall duration of the vulva redness and/or the intensity of this redness.

Practically, the memory 41 and comparison block 42 can be made in the form of a suitably programmed conventional PC.

Advantageously, the redness measurement can be of the relative type; i.e. changes in the blood volume can be taken into account. For an analysis of this type, during an initial learning step of the system it is necessary to evaluate the specific basal level for each animal; the final measurement value therefore will state the amount of the variation relative to the basal level.

Since changes in the vulva colour are a characteristic sign of the pro-oestrus/oestrus phase and the estrogens in circulation, it is apparent that monitoring of these changes—and highlighting of the relations with some characteristic hormones such as estrogens and/or progesterone—represent a very useful element for planning of artificial insemination.

FIG. 2 is a diagram showing the relation between the vagina redness scale and the development of the animal's oestrus cycle; in particular, the upper part of the graph shows the time on the x axis and the redness amount on the y axis.

As can be seen, the interval of greater redness occurs immediately before ovulation, i.e. the period of the animal's maximum fertility.

The processing unit 40—and in particular the comparison block 42—is therefore set to generate a suitable notification signal 50, should a predetermined mammal be close to its fertile period.

The notification signal for example can activate a signal of the visual and/or sound type.

Advantageously, the reproductive status of the mammal is determined by the processing unit 40 depending on the colour taken by the mammal's vagina wall, which is representative of the amount of blood perfused in the predetermined region Z of the vagina canal.

For example, an infra-red radiation can be emitted and the corresponding radiation reflected by the region Z be detected, for determining changes of the vagina canal redness; preferably the IR radiation has a wavelength comprised between 760 nm and 1400 nm, in particular between 800 nm and 820 nm (for example equal to 810 nm) or between 950 nm and 970 nm (for example equal to 960 nm).

As an alternative, a red radiation can be employed; such radiation may have a wavelength included between 500 nm and 760 nm, preferably between 600 nm and 760 nm, for example equal to 640 nm.

In case a single wavelength is used, the intensity of the radiation is considered directly as a measure of the vagina canal's redness, without further substantial processing.

The reproductive status of the mammal can also be determined by the processing unit 40 based on a comparison between the chromatic components defining such the colour of the vagina's wall.

The chromatic components can be components of different wavelengths of the same electromagnetic radiation, or separate radiation emissions of different wavelengths.

According to a first embodiment, said wavelengths comprise a first wavelength included between 760 nm and 1400 nm, i.e. the first wavelength falls within the infrared range; preferably, the first wavelength is comprised between 800 nm and 820 nm (for example, equal to 810 nm) or between 950 nm and 970 nm (for example, equal to 960 nm). According to the same first embodiment said wavelengths further comprise at least one second wavelength different than said first wavelength and preferably included between 400 nm and 760 nm, in particular between 500 and 760 nm, and more preferably between 600 nm and 760 nm. For example the second wavelength can be equal to 640 nm.

Preferably said wavelengths further comprise a third wavelength different from said first and second wavelengths; the third wavelength may be included between 490 nm and 600 nm.

In a preferred embodiment, the second and third wavelengths may identify complementary colours, so that the oestrus cycle of the mammal is determined as a function of an IR radiation (first wavelength) and of a couple of complementary colours (second and third wavelengths).

According to a second embodiment, the first and the second wavelengths identify complementary colours, the first wavelength being included between 500 nm and 760 nm (practically, red or green).

In a further embodiment, the first wavelength may be included between 630 nm and 760 nm (red), the second wavelength may be included between 500 nm and 570 nm (green) and the third wavelength may be comprised between 410 nm and 490 nm (blue).

By comparing the radiation emissions or the components at the first and second wavelengths, following detection of variations in the intensity of the individual wavelengths, the following events can appear:

the radiation emissions or components are submitted to variations that are "concordant", i.e. the different intensities vary following the same course, for instance according to the same proportionality factor (the intensities of the different radiation emissions or components all increase by a factor of 1.5, for example); this means that there has been no variation in the colour of the mammal's vagina wall, but that merely the detecting means has moved closer (intensity increase) or farther (intensity decrease) with respect to the vagina wall, as a result of a movement of the animal, for example;

the radiation emissions or components are submitted to variations that are "discordant", i.e. the different intensities vary following different courses, for instance according to different proportionality factors (the radiation or component at the first wavelength increases by a factor of 1.5 while the radiation or component at the second wavelength keeps substantially unchanged, for example); this means that there has been a change in the colour of the mammal's vagina wall, and in particular the intensity increase of the red component reveals beginning of the animal's fertile period.

By way of example, the comparison between the radiation emissions or components at different wavelengths can take place through calculation of the ratio between the intensities of said radiation emissions or components.

Should two of said wavelength identify complementary colours, the comparison between the intensities may be carried out by comparing the variation of intensity of the first wavelength with the variation of intensity of the radiation obtained from the sum (or superposition) of said complementary colours.

In practice, the variation of intensity of the first wavelength is compared with the variation of intensity of white/grey/black given by the sum of the complementary colours.

In this case too, the oestrus cycle is determined as a function of "concordant" or "discordant" variations.

Clearly, should also a radiation or component to the third wavelength be taken into account, the above speech is also extended in the same manner to this radiation or component too.

It is to be noted that the first wavelength (IR radiation in the first embodiment, red-green in the second embodiment, red in the third embodiment) can be representative of the redness of the region Z of the vagina canal; the second, and preferably third wavelength, can be used to determine whether variations of intensities of the first wavelength correspond to variations of the vagina redness or to mere movements of the sensor 11.

Such information may clearly be obtained also in case the intensity of the first wavelength does not vary, whereas the intensity of the second (and/or third) wavelength changes.

As an alternative, in the first embodiment the second wavelength (preferably when included between 600 nm and 760 nm) can be representative of the redness of the vagina canal, whereas the first and possibly the third wavelength are used to determine whether a change in the vagina canal's redness has occurred.

For carrying out this type of analysis, sensor 11 is provided with an emitter element 100 to generate at least one electromagnetic radiation R1 directed onto the predetermined region Z of the mammal's vagina wall; thus a corresponding reflected radiation R2 is obtained.

Sensor 11 further comprises a receiver element 120 to receive said reflected radiation from the predetermined region Z of the vagina wall; then the main signal 20 is generated depending on the reflected radiation R2 received from the receiver element 120.

As stated above, according to a basic but effective embodiment, only one wavelength may be employed. Said wavelength can fall in the infra-red range (760 nm-1400 nm, preferably 800 nm-820 nm or 950 nm-970 nm, for example equal to 810 nm or 960 nm) or in the red light range (500 nm-760 nm, preferably 600 nm-760 nm, for example equal to 640 nm).

In case two or more wavelengths are taken into account for determining the reproductive status of the mammal, two embodiments are envisaged.

According to a first embodiment (FIG. 13), the emitter element 100 generates an electromagnetic radiation having components of different wavelengths, and in particular a first component having a wavelength included between 760 nm and 1400 nm, and at least one second component included between 400 nm and 760 nm.

Preferably the second component has a wavelength included between 500 nm and 760 nm, in particular between 600 nm and 760 nm, for example equal to 640 nm.

Preferably, the electromagnetic radiation comprises a third component of a wavelength included between 490 nm and 600 nm.

The receiver element 120 comprises a first detector 121 adapted to detect electromagnetic radiation emissions of wavelengths included between 760 nm and 1400 nm, and at least one second detector 122 adapted to detect electromagnetic radiation emissions of wavelengths included between 400 nm and 760 nm, in particular between 500 nm and 760 nm, and more preferably between 600 nm and 760 nm—for example 640 nm.

Preferably the receiver element further comprises a third detector 123, adapted to detect radiation emissions having a wavelength included between 490 nm and 600 nm.

As an alternative, the first wavelength may be comprised between 500 nm and 760 nm, and the second wavelength can identify the complementar colour of the colour associated to the first wavelength, the second wavelength being included between 410 nm and 500 nm.

As a further alternative, the first wavelength may be included between 630 nm and 760 nm (red), the second wavelength may be included between 500 nm and 570 nm (green) and the third wavelength may be comprises between 410 nm and 490 nm (blue).

By way of example, each detector may comprise an inlet filter F to filter the entering radiation and selecting the range of wavelengths that must be received, and a photosensitive device such as a photodiode D, to convert the received light radiation into an electric signal.

Preferably, each detector comprises a 3×3 matrix of photodiodes, to improve reception and reduce noise and inaccuracy due to the animal's movements.

However it is to be appreciated that any kind of suitable sensor can be used to detect said reflected radiation; for example, even a small camera can be employed.

In the first embodiment therefore, the radiation striking on the vagina wall comprises all components of interest (it can be a white light, for example) and, after the radiation has been reflected by the vagina wall, the individual components are filtered by the receiver element 120, by means of the above described structure.

A managing unit 80b carries out incorporation of the parameters of interest (intensity) of the individual components into the main signal 20 and transmission of the main signal 20 to the processing unit 40 for subsequent processing operations.

The processing unit 40 compares with each other the intensities of the different components selected, so as to determine the reproductive status of the mammal under examination.

In a second embodiment (FIG. 14), the emitter element 100 comprises a first emitting device 101 to generate a first electromagnetic radiation to a first wavelength included in the range of 760 nm to 1400 nm, and at least one second emitting device 102 to generate a second electromagnetic radiation to a second wavelength included between 400 nm and 760 nm.

Preferably the second wavelength is included between 500 nm and 760 nm, in particular between 600 nm and 760 nm—for example equal to 640 nm.

Preferably, the emitter element 100 comprises a third emitting device 103 to generate a third electromagnetic radiation to a third wavelength included between 490 nm and 600 nm.

Preferably, the emitter element 100 comprises a couple of emitting devices for each radiation (i.e. for each wavelength). In case only the first and second wavelengths are used, the emitter element 100 may comprise three emitting devices for each wavelength.

In case also the third wavelength is used, two emitting devices for each wavelength are provided.

Therefore the emitter element 100 may comprise six emitting devices, alternately positioned at the vertices of an equilateral hexagon, so that between each couple of equal emitting devices at least one different emitting device is positioned. Preferably, within said hexagon is positioned the receiver element 120 (in particular the detector 120a that will be disclosed hereinafter).

In the second embodiment the receiver element 120 comprises a detector 120a capable of detecting electromagnetic radiation emissions to said first wavelength and said second wavelength; should the emitter element 100 be provided with said third emitter device 103, the detector 120a of the receiver element 120 is set to detect radiation emissions to the third wavelength too.

As an alternative, the receiver 120 may comprise two or more specific detectors (not shown), each adapted to detect a wavelength emitted by a respective emitting device; said specific detectors are preferably arranged alternatively according to a "chess board" structure, so as to achieve a uniform detection of such wavelength.

The detecting means 10 further comprises a control unit 80a, operatively associated with the emitting devices to selectively drive the latter and cause, at different time intervals, electromagnetic radiation emissions to different wavelengths.

In other words, the control unit 80a activates the emitting devices in succession, so that the radiation emissions to the first wavelength are generated at different instants relative to the radiation emissions to the second wavelength, and to the radiation emissions to the third wavelength, should the third emitting device be provided as well.

All the reflected radiation emissions generated by radiation to the first, second and preferably third wavelengths are received by the same detector 120a (or by the aforementioned specific detectors).

The main signal 20 is representative of the radiation intensities to wavelengths different from each other received by detector 120a (or specific detectors).

The processing unit 40, operatively associated with said detector 120a or specific detectors, being known the time instants (or intervals) at which the individual radiation emissions are generated, is able to determine the intensity of each reflected radiation and to establish to which incident radiation (i.e. which wavelength) this intensity corresponds.

Therefore by applying the above described technique for comparison between the intensities to the different wavelengths, the animal's reproductive status is determined.

It is to be pointed out that, due to the hitherto described structure, several animals can be simultaneously monitored, so that the work of the staff in charge is greatly reduced.

In particular, each animal under observation can be associated with a respective interface 21 which is set to communicate with the detecting means 10 introduced into the vagina canal of such an animal; the different interfaces 21 are also connected with a single processing unit 40 performing the operations for determining the animals' oestrus cycle in a centralised manner.

As above said, connection between the detecting means 10 and the respective interface can be obtained both through a suitable wiring, and through wireless technologies (bluetooth, for example).

Therefore, the detecting means 10 can be provided with a rechargeable portable power unit (suitably sized batteries, for example) to enable correct detection even in the absence of connection through wires with the rest of apparatus 1.

In addition to the above, the detecting means 10 may be provided to perform a "double reading" of the inner wall of the animal's vagina canal; in other words, this detecting means 10 may comprise a pair of sensors carrying out detecting operations on opposite sides of the vagina canal.

Practically, in the housing 14 two plethysmographic sensors are mounted that face different portions of the vagina canal, and in particular opposite surfaces thereof.

In this case two signals are simultaneously acquired, and the detected data will be taken into account by the processing unit 40 only if the two distinct detecting operations supply values that are consistent with each other.

From the point of view of operation, the following is to be pointed out.

First of all, the detecting means 10 is inserted at least partly into the mammal's vagina canal and such fastened that the detecting operations carried out can be precise and reliable.

To this aim, the above stated steps can be performed as regards the fastening means 30 (main body 31, contact element 32, closing member 33, and possibly auxiliary contact element 32').

Then the blood amount perfused in a predetermined region of the animal's vagina canal is detected; this detection preferably takes place through a sensor, in particular of the plethysmographic type, adapted to detect redness of the inner vulva wall.

To perform this detection an infra-red radiation can be used, having a wavelength preferably included between 760 nm and 1400 nm, in particular included between 800 nm and 820 nm (for example equal to 810 nm) or between 950 nm and 970 nm (for example equal to 960 nm); alternatively a red radiation can be used, included between 500 nm and 760 nm, preferably between 600 nm and 760 nm, for example equal to 640 nm.

In case a single wavelength is used, the intensity of the radiation is considered directly as a measure of the vagina canal's redness, without further substantial processing.

According to a more complex technique, a comparison step is preferably carried out between the radiation emissions or radiation components to different wavelengths reflected from the predetermined region Z of the mammal's vagina canal, the reproductive status of said mammal being determined depending on said comparison.

In particular, said different wavelengths comprise:
a first wavelength included in the range of 760 nm to 1400 nm;
at least one second wavelength included between 400 nm and 760 nm.

As pointed out above, preferably the second wavelength is included between 500 nm and 760 nm, and in particular between 600 nm and 760 nm—for example equal to 640 nm.

Advantageously, the wavelengths different from each other also comprise a third wavelength included between 490 nm and 600 nm.

Generally, at least one electromagnetic radiation is generated that is directed to the predetermined region Z to obtain a corresponding reflected radiation, so that the main signal is generated depending on this reflected radiation.

In accordance with a first embodiment of the process, the electromagnetic radiation comprises at least one first and one second wavelengths, the first wavelength being included in the range of 760 nm to 1400 nm, while the second wavelength is included between 400 nm and 760 nm.

The second wavelength can be included between 500 nm and 760 nm, preferably between 600 nm and 760 nm, in particular equal to 640 nm.

The electromagnetic radiation may also comprise a third wavelength included between 490 nm and 600 nm.

During the receiving step, filtering of a first component to the first wavelength, of a second component to the second wavelength and preferably of a third component to the third wavelength is carried out.

The mammal's reproductive status is therefore determined depending on a comparison between said components.

As an alternative, the first wavelength may be comprised between 500 nm and 760 nm, and the second wavelength can identify the complementar colour of the colour associated to the first wavelength, the second wavelength being included between 410 nm and 500 nm.

As a further alternative, the first wavelength may be included between 630 nm and 760 nm (red), the second wavelength may be included between 500 nm and 570 nm (green) and the third wavelength may be comprises between 410 nm and 490 nm (blue).

In accordance with a second embodiment of the process, a first electromagnetic radiation to a first wavelength included between 760 nm and 1400 nm and a second electromagnetic radiation to a second wavelength included between 400 nm and 760 nm are generated, preferably between 500 nm and 760 nm, in particular between 600 nm and 760 nm.

Preferably also a third electromagnetic radiation to a third wavelength included between 490 nm and 600 nm is generated.

Advantageously, the first and second electromagnetic radiation (and preferably the third electromagnetic radiation) are selectively generated within different time intervals, so that at each time instant only one electromagnetic radiation is generated.

The mammal's reproductive status is then determined depending on a comparison between at least one reflected radiation generated by an electromagnetic radiation to the first wavelength and at least one reflected radiation generated by an electromagnetic radiation to the second wavelength.

Preferably, included in the comparison step is also a reflected radiation generated by an electromagnetic radiation to the third wavelength.

As an alternative, the first wavelength may be comprised between 500 nm and 760 nm, and the second wavelength can identify the complementar colour of the colour associated to the first wavelength, the second wavelength being included between 410 nm and 500 nm.

As a further alternative, the first wavelength may be included between 630 nm and 760 nm (red), the second wavelength may be included between 500 nm and 570 nm (green) and the third wavelength may be comprises between 410 nm and 490 nm (blue).

Following the above detection, a main signal 20 is generated that is representative of said perfused blood amount and/or of the redness of the vagina wall portion facing the detecting means 10.

The main signal 20 is compared with one or more prestored parameters which are the reference parameters 41*a* for the reproductive status of the animal under examination.

Preferably the reference parameters 41a comprise parameters representative of the animal's basal level, detected during an initial learning step of the system.

Depending on this comparison the mammal's reproductive status is determined; in particular, a notification signal 50, advantageously of the visual and/or sound type, is generated to draw the operator's attention to the forthcoming fertility period of the animal.

The invention achieves important advantages.

First of all, the apparatus and method of the invention enable the artificial insemination activity of mammals kept for breeding to be programmed in a precise and reliable manner.

In addition, exactly by virtue of the system reliability, the costs connected with insemination are minimised and the birthrate of new animals is optimised.

Another advantage is found in the fact that, during the detecting step, the detecting means is fastened in the vagina canal in a substantially irremovable manner, thus increasing measurement accuracy.

The invention claimed is:

1. A method of detecting a reproductive status of a non-human animal which undergoes oestrus, said method comprising the following steps:
    detecting a blood amount perfused in a predetermined region of a vaginal canal of said animal by:
    illuminating said predetermined region with a first electromagnetic radiation having a first wavelength between 760 nm and 1400 nm, a second electromagnetic radiation having a second wavelength between 600 nm and 760 nm, and a third electromagnetic radiation having a third wavelength between 490 nm and 600 nm,
    receiving a reflected radiation of each of said first, second and third radiations from said region,
    obtaining values for each of said reflected radiations,
    comparing using a processing unit said values for each of said reflected radiations with each other and comparing, using said processing unit, said values from said first, second, and third wavelengths with, respectively, values predetermined from reflected radiations of said first, second, and third wavelengths, the predetermined values being typical of said animal's vulva during an oestrus period; and
    determining using a processing unit a reproductive status of said animal depending on said comparisons.

2. A method as claimed in claim 1, further comprising a step of inserting detecting means into said animal's vaginal canal for detecting said blood amount.

3. A method as claimed in claim 1, wherein said first and second electromagnetic radiations are generated in different time intervals.

4. A method according to claim 1, wherein the comparison step between the radiation emissions or components at different wavelengths includes calculating ratios between the intensities of said reflected radiations.

5. A method according to claim 2, wherein the first wavelength is representative of vaginal redness of the region of the vaginal canal, and the second and the third wavelengths are used to determine whether the variations of intensities of the first wavelength correspond to variations of said vaginal redness or mere movements of the detecting means.

* * * * *